(12) United States Patent
Shirvan et al.

(10) Patent No.: US 8,574,902 B2
(45) Date of Patent: Nov. 5, 2013

(54) ACTIVATED LEUKOCYTE COMPOSITION AND USES FOR WOUND HEALING

(75) Inventors: Mitchell Shirvan, Herzliyya (IL); Eilat Shinar, Jerusalem (IL); Orit Frenkel, Tel Hashomer (IL); Adi Zuloff-Shani, Herzliyya (IL); Marina Bubis, Rehovot (IL); Eilat Bain, Rehovot (IL); Irene Ginis, Beit Shemesh (IL)

(73) Assignee: Macrocure Ltd., Petach Tikva (IL)

( * ) Notice: Subject to any disclaimer, the term of this patent is extended or adjusted under 35 U.S.C. 154(b) by 66 days.

(21) Appl. No.: 13/224,946

(22) Filed: Sep. 2, 2011

(65) Prior Publication Data

US 2012/0058156 A1 Mar. 8, 2012

Related U.S. Application Data

(63) Continuation-in-part of application No. PCT/IB2010/000882, filed on Mar. 5, 2010.

(60) Provisional application No. 61/209,298, filed on Mar. 5, 2009, provisional application No. 61/211,587, filed on Apr. 1, 2009, provisional application No. 61/381,268, filed on Sep. 9, 2010, provisional application No. 61/460,024, filed on Dec. 23, 2010.

(51) Int. Cl.
  *C12N 5/08* (2006.01)
  *C12N 5/00* (2006.01)
  *C12N 5/02* (2006.01)

(52) U.S. Cl.
  USPC ............................ 435/373; 435/377; 435/383

(58) Field of Classification Search
  None
  See application file for complete search history.

(56) References Cited

U.S. PATENT DOCUMENTS 6,146,890 A  11/2000  Danon

FOREIGN PATENT DOCUMENTS

| GB | 2 146 523 | 4/1985 |
|---|---|---|
| WO | WO 00/69449 | 11/2000 |
| WO | WO 2008/155659 | 12/2008 |
| WO | WO 2010/100570 | 9/2010 |

OTHER PUBLICATIONS

Fonder et al., "Treating the Chronic Wound: A Practical Approach to the Care of Nonhealing Wounds and Wound Care Dressings," *Journal of the American Academy of Dermatology*, Feb. 2008, pp. 185-206.
Frenkel et al., "Activation of Human Monocytes/Macrophages by Hypo-Osmotic Shock," *Clinical and Experimental Immunology*, vol. 124, No. 1, Apr. 2001, XP009157316, pp. 103-109.
Werner et al., "Regulation of Wound Healing by Growth Factors and Cytokines," *Physiological Reviews*, vol. 83, No. 3, Jul. 2003, XP-002672025, pp. 835-872.
International Search Report and Written Opinion, dated Apr. 26, 2012, for International Application No. PCT/IB2011/002756 (14 pages).
International Search Report and Written Opinion in PCT/IB2010/000882, filed Mar. 5, 2010.

*Primary Examiner* — Michail Belyavskyi
(74) *Attorney, Agent, or Firm* — Finnegan, Henderson, Farabow, Garrett & Dunner, LLP

(57) ABSTRACT

Disclosed are therapeutic, blood-derived activated leukocyte compositions, methods of making them, and methods of using the compositions to repair or promote the prevention and healing of wounds.

12 Claims, 5 Drawing Sheets

↓ Sterile Connecting Device

Figure 3A: CD62L Expression
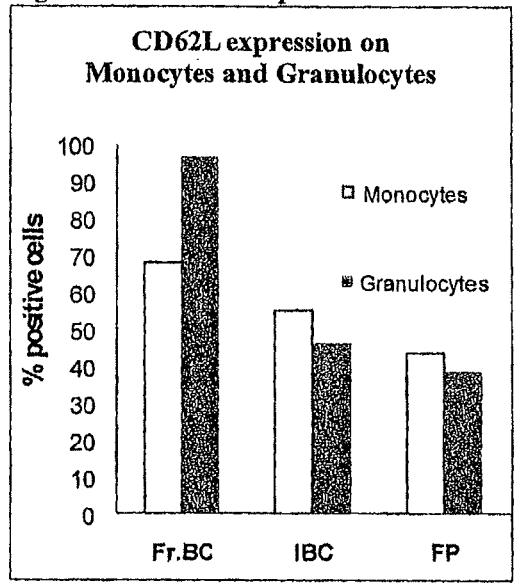
Figure 3B: CD42b Expression
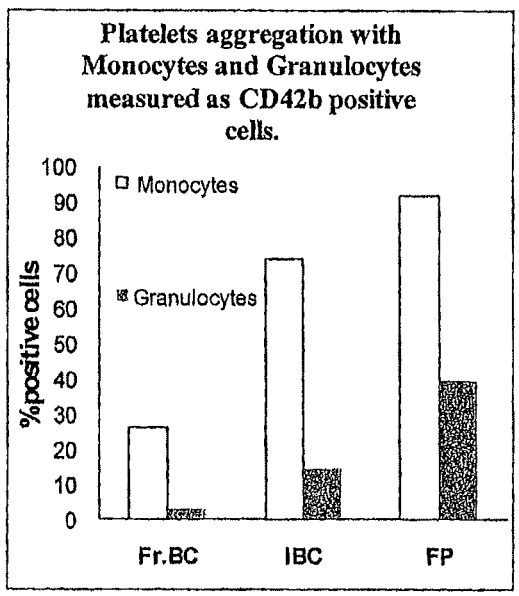

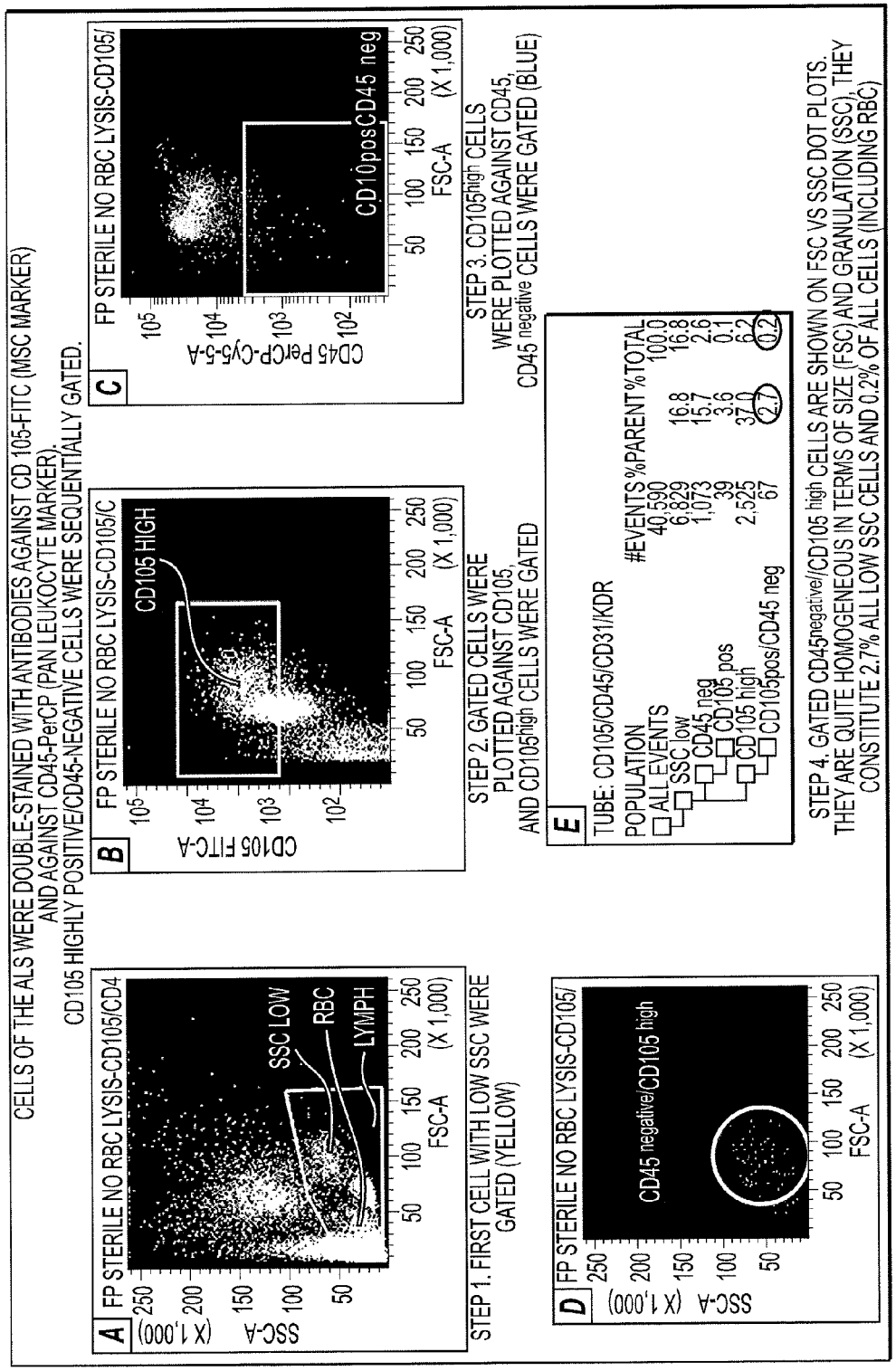

ACTIVATED LEUKOCYTE COMPOSITION AND USES FOR WOUND HEALING

CROSS-REFERENCE TO RELATED APPLICATIONS

This application is a continuation-in-part of International Application No. PCT/IB2010/000882, filed Mar. 5, 2010, in English and designating the United States, which claims benefit of Provisional Application Ser. No. 61/209,298, filed Mar. 5, 2009, and Provisional Application Ser. No. 61/211,587, filed Apr. 1, 2009, the disclosures of each of which are hereby incorporated herein by reference. This application also claims benefit of Provisional Application Ser. No. 61/381,268, filed Sep. 9, 2010, and Provisional Application Ser. No. 61/460,024, filed Dec. 23, 2010, the disclosures of each of which are also incorporated herein by reference.

BACKGROUND OF THE INVENTION

The wound healing process involves participation of white blood cells, also known as leukocytes. Leukocytes include lymphocytes, granulocytes and monocytes. Three common types of lymphocytes are T-cells, B-cells and natural killer cells. T-cells and B-cells play important roles in the recognition of antigens in the body (Parkin, 2001). Natural killer (NK) cells identify infected cells by alterations in the levels of the major histocompatability complex (MHC), and destroy the infected cells (Moretta, 2008). The participation of lymphocytes in the healing process is largely associated with their production of cytokines and growth factors (Keen, 2008). A new class of gamma-delta-T cells has been described in the skin (Jameson, 2002. Havran, 2005). Among the different types of granulocytes are neutrophils, basophils and eosinophils. Monocytes differentiate into macrophages, which are responsible for destruction of tissue debris or invading foreign substances. Macrophages also produce molecules that control inflammation and repair (Riches, 1996).

The process of wound healing occurs in three overlapping phases. (Li, 2007; Broughton, 2006; Tsirogianni, 2006; Singer, 1999; Martin, 1997). The first phase is the inflammatory phase. It is characterized by recruitment of neutrophils, followed by monocytes to the wound site, where they kill and phagocytize bacteria (Agaiby, 1999).

The second wound healing phase which is known as the proliferative phase, involves formation of new granulation tissue. Fibroblasts proliferate and migrate into the wound space and synthesize collagen and other components of extra-cellular matrix (Greiling, 1997). At the same time, angiogenesis occurs, providing nutrients and oxygen to the metabolically active new granulation tissue (Tonnesen, 2000). Keratinocytes from the intact epidermis start to migrate over the provisional matrix and begin to proliferate, leading the way for new epithelial tissue (Kim, 1992).

Remodeling is the third and final phase in wound healing. It is characterized by fibroblast differentiation into myofibroblasts, which contract and bring the wound edges closer together (Tomasek, 2002). Remodeling of the collagen fibers by degradation and re-synthesis allows the wound to gain strength by re-orientation of the collagen fibers (a process tightly controlled by growth factors) (Werner, 2003).

The challenge of treating wounds is often compounded by patients with multiple pathologies such as diabetes, coronary artery disease and hypertension. These diseases have the common effect of exacerbating vascular complications due to various physiological conditions. Complications from wounds may result in increased morbidity and mortality (Doshi, 2008).

Conventional wound treatments include surgical debridement, antibiotic therapies and various dressings (Moran, 2008; Fonder, 2008). Wounds resistant to conventional treatment are also referred to as refractory wounds. These wounds lead to a decrease in quality of life and can result in increased morbidity and mortality. Thus, a need continues to exist for effective wound healing compositions and methods.

BRIEF SUMMARY OF THE INVENTION

One aspect of the present invention is directed to a method for making an activated leukocyte composition (ALC) derived from blood (e.g., obtainable or obtained from a whole blood sample). The method includes the steps of subjecting leukocytes, which may be obtained from a sample of whole human blood, to a first incubation for a period of time and at a temperature which allows the leukocytes to become activated, which in preferred embodiments, is about 8 to about 20 hours, and at room temperature. After incubation, the leukocytes are contacted with a physiologically acceptable aqueous solution such as sterile, distilled water, to initiate hypo-osmotic shock, followed by contacting the shocked leukocytes with a physiologically acceptable salt solution to restore isotonicity. This activated leukocyte composition (ALC) may be used therapeutically. However, in some embodiments, separate and substantially concurrent with the first incubation of the leukocytes, a sample of plasma, which may be obtained from the same or different whole blood sample (i.e., from the same or a different human), is contacted with a coagulating agent at about 37° C. concurrent with the leukocyte incubation, which in preferred embodiments, is about 8 to about 20 hours, followed by separating serum from the coagulated plasma sample. The leukocytes are re-suspended in serum collected from the coagulated plasma sample, thus forming the ALC. After the first incubation, the leukocytes may be further subjected to a second incubation for about 60 to about 120 minutes at about 37° C.

Thus, in one aspect the invention provides a method for making an activated leukocyte composition comprising: a) incubating human leukocytes for a period of time so that the leukocytes transition from a quiescent to a functionally active state; b) subjecting the leukocytes to hypo-osmotic shock; and c) adding to the leukocytes of step b) a salt solution in an amount which restores isotonicity. In some embodiments, the method further comprises mixing the activated leukocytes of step c) with serum.

In another aspect the invention provides a method for activating leukocytes comprising: a) obtaining leukocytes from human blood; and b) incubating the human leukocytes for a period of time so that the leukocytes transition from a quiescent to a functionally active state.

In some embodiments of these aspects, the incubation of step a) occurs at a temperature of about 12° C. to about 28° C. for a time ranging from about 8 to about 20 hours. In some embodiments, the incubation of step a) occurs at a temperature of about 18° C. to about 24° C. for a time ranging from about 8 to about 12 hours. In other embodiments, the incubation of step a) occurs at a temperature of 12° C. to about 28° C. for a time ranging from about 90 minutes upwards of 2, 3, 4, 5, 6, 7, 8, or 12 to about 20 hours. In other embodiments, the incubation of step a) occurs at a temperature up to about 37° C. and for a time ranging from five hours to about 24 hours.

In some embodiments, the activated leukocyte composition has a shelf life extending up to 97 hours following collection of the human leukocytes.

In some embodiments, the human leukocytes are obtained from a donor having an O negative blood type.

In some embodiments, the hypo-osmotic shock comprises contacting the leukocytes with water.

In some of those embodiments further comprising mixing the activated leukocytes with serum, the serum is prepared from plasma obtained from a donor having AB positive blood type. Also, in some of those embodiments further comprising mixing the activated leukocytes with serum, the mixture of activated leukocytes and serum is incubated at about 37° C. for about 8-20 hours. In other embodiments, the mixture of activated leukocytes and serum is incubated for about 60 to about 120 minutes.

In other aspects, the invention provides a composition comprising activated leukocytes made according to any of the methods of the invention described herein.

Another aspect of the present invention is directed to an ALC derived from blood. The activated leukocyte composition of the present invention includes, in terms of the population of leukocytes present therein, about 40% to about 90% granulocytes, about 5% to about 20% monocytes and about 5% to about 30% lymphocytes, based on the total number of leukocytes in the ALC. As shown in the working examples, the inventive ALCs may also be characterized and distinguished from known compositions in terms of minimum yield of leukocytes (relative to the whole blood sample), viability of leukocytes, and minimum activation levels of granulocytes, e.g., as indicated by CD11b. The ALC may further contain residual levels of platelets (in amounts of about $46.8+/-39.2(10^3/\mu l)$ and red blood cells (in the amount of about $0.1+/-0.06(10^6/\mu l)$ of the ALC. The population of granulocytes may include about 52% to about 78% neutrophils; about 1% to about 9% eosinophils; and about 1% to about 2% basophils. The population of lymphocytes may include about 7% to about 25% B cells (CD19+), about 20% to about 30% NK cells (CD3−/CD56+), about 40% to about 60% T cells (CD3+), about 0%, for example, about 0.1%, to about 30% of NKT cells CD3+/CD56+, about 8% to about 20% of T helper cells (CD4+/CD3+), and about 20% to about 30% of CD8+/CD3+ cells.

In some embodiments, the composition includes T-helper cells and T-suppressor cells in a ratio of less than 0.8.

In some embodiments, the composition further comprises mesenchymal stem cells in an amount ranging from about 0.1% to about 5.0% of the total cell population in the composition.

In some embodiments, the composition further comprises endothelial progenitor cells in a amount ranging from about 0.1% to about 5.0% of the total cell population in the composition.

The cells may be suspended in a carrier such as serum (which may be autologous or allogeneic with respect to recipient) or some other physiologically acceptable iso-normal liquid suitable for storing and administering cells, such as the solution used to restore isotonicity.

Another aspect of the invention relates to articles of manufacture comprising a composition of the invention and a dressing. In some embodiments, the dressing is a dry dressing, moisture-keeping barrier dressing, or bioactive dressing. In those embodiments involving a dry dressing, the dressing may be a gauze, a bandage, a non-adhesive mesh, a membrane, foils, foam, or a tissue adhesive. In those embodiments involving a moisture-keeping barrier dressing, the dressing may be a paste, a cream, an ointment, a nonpermeable or semi-permeable membrane or foil, a hydrocolloid, a hydrogel, or combinations thereof. In those embodiments involving a bioactive dressing, the dressing may be an antimicrobial dressing.

In still another aspect, a composition of the invention may further comprise as a matrix or scaffold a material suitable for implantation in a person. In some embodiments, the material is a solid before implantation. In some embodiments, the material is a gel that solidifies following implantation.

Yet another aspect of the present invention is directed to a method of promoting wound healing or of treating a wound, which includes administering or otherwise applying the ALC to a wound. In some embodiments, the wound is a decubital ulcer, a pressure ulcer, a lower extremity ulcer, a deep sternal wound, a post-operative wound, a refractory post-operative wound of the trunk area, a wound to the great saphenous vein following harvesting of the great saphenous vein, a venous ulcer, or an anal fissure. In those embodiments involving a lower extremity ulcer, the ulcer may be in a diabetic patient. In other embodiments, the wound is a venous ulcer, pressure ulcer, or post-operative ulcer.

In other aspects, the invention is directed to a method of inhibiting the onset of infection in a wound, comprising administering to the wound a composition of the invention. In one embodiment, the wound is caused by trauma. In another embodiment, the wound is caused by surgery.

In those aspects involving methods of treating a wound, the wound may also be treated by administering to the wound an article of manufacture comprising a composition of the invention.

For purposes of the present invention, wounds include tattoos. Accordingly, a further aspect of the present invention is directed to a method of tattoo removal, which includes administering or otherwise applying the ALC or an article of manufacture comprising the ALC, to a tattoo.

The disclosed invention achieves several unexpected results compared to at least one known wound healing composition containing white blood cells. As demonstrated in working examples herein, these results include increased yield and viability of leukocytes (WBCs), higher percentage of activated granulocytes, and the presence of unexpectedly high concentrations of mesenchymal stem cells and endothelial progenitor cells. The disclosed invention is also believed to include an unexpectedly and relatively high percentage of activated monocytes (compared to blood) and a relatively higher percentage of CD8 T-cells compared to CD4 T-cells.

BRIEF DESCRIPTION OF THE DRAWINGS

FIGS. 3A and 3B are graphs illustrating the general trends of both CD62L and CD42b expression, which are indicators of cell activation.

FIGS. 4A-4E demonstrate the results of identification of mesenchymal stem cells (MSC) in ALS using flow cytometry analysis. FIGS. 4A-4D are dot plot graphs illustrating the sequential steps of gradually narrowing (gating) cell population containing MSC, ending with a practically homogenous (in terms of size and surface character) population of cells negative for the common marker of leukocytes (CD45) and bearing MSC marker CD105. FIG. 4E depicts statistical analysis of sequentially gated populations, demonstrating that the final population of CD 105 positive/CD45 negative cells composes 2.7% of CD105 highly positive cells and 0.2% of all cells in the tested ALS sample.

FIG. 5B depicts a control experiment: a similar dot plot graph, where cells of ALS were stained with irrelevant but isotype-matched antibodies. No positively-stained cells were found.

DETAILED DESCRIPTION OF THE INVENTION

Figure 1:
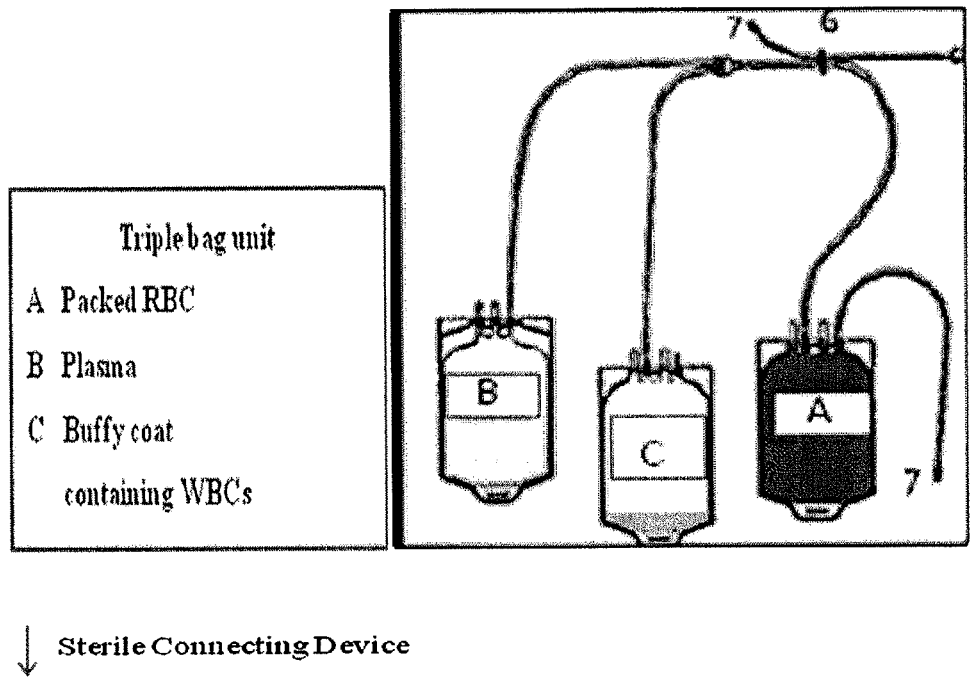
FIG. 1 schematically depicts a first portion of a representative system for producing the ALC compositions of the present invention, which includes bags A-C (Set-1), which are blood storage bags or containers, wherein bag A contains packed red blood cells collected from a donor; bag B contains plasma; and bag C contains leukocytes (which following initial separation from whole blood form a layer commonly referred to as the buffy coat).

Blood is defined herein as whole blood or any of its constituent parts (e.g., plasma, leukocytes, platelets or red blood cells). The amounts of platelets and red blood cells that may be present in the ALC of the present invention may be lower than that in whole blood.

The term "about" as used herein in connection with any and all values (including lower and upper ends of numerical ranges) as any value having an acceptable range of deviation of +/−0.5% to +/−20% (and values therebetween, e.g., ±1%, ±1.5%, +2%, ±2.5%, ±3%, ±3.5%, ±4%, ±4.5%, ±5%, ±5.5%, +6%, ±6.5%, ±7%, ±7.5%, ±8%, ±8.5%, ±9%, ±9.5%, ±10%, ±10.5%, ±11%, ±11.5%, ±12%, ±12.5%, ±13, ±13.5%, ±14%, ±14.5%, ±15%, ±15.5%, +16%, ±16.5%, +17%, +17.5%, ±18%, ±18.5%, ±19%, ±19.5%, and ±20%).

The starting materials for producing the inventive ALCs may be obtained from several sources. Whole blood or one or more components thereof (e.g., leukocytes and plasma) may be obtained from autologous or allogeneic sources. In one embodiment of the present invention, the blood sample is collected from the patient who will ultimately be treated with the ALC, which is referred to herein as an autologous blood sample or source. In embodiments wherein the source(s) i.e., the blood or its components, is obtained from an individual other than the intended ALC recipient, which is referred to as an allogeneic blood sample or source, these starting materials may be conveniently obtained from a blood bank. The samples may be screened by the blood bank for blood type (ABO, Rh), irregular antibodies to red cell antigens, and transfusion-transmittable diseases. More specifically, screening can be conducted with antibodies using an Abbott PRISM instrument against: Hepatitis B, C, HIV ½, HTLV and Syphilis (−HCV; HbsAg; anti-HIV ½ O+; and anti-HTLV I/II). The samples can also be screened for HIV, HCV and HBV by molecular methods (NAT-Nucleic Acid Testing). Molecular screening can be accomplished using commercially available instrumentation, e.g., the TIGRIS system of Chiron.

In these embodiments involving allogeneic sources, the samples can be obtained from donors with the same blood type as the intended ALC recipient. Alternatively and as further described herein, plasma samples can be obtained from donors with AB+ blood and the leukocytes can be obtained from patients with O− blood. Patients with AB+ blood are universal donors for plasma and patients with O− blood are universal donors for leukocytes. In still other embodiments, the leukocytes and/or plasma may be of any blood type. The plasma used in the invention can be fresh, stored (e.g., at 1-6° C. for less than 24 hours), dried, or otherwise pre-treated (e.g., pathogen-reduced plasma and solvent/detergent (SD) treated plasma). The plasma can be fresh or stored at 1-6° C. for less than 24 hours, or Fresh Frozen Plasma, or Dried Plasma, or Pathogen-Reduced Plasma, or Solvent/Detergent (SD) Treated Plasma. Regardless of the source, all necessary processing of the sample(s) can be carried out without the need for highly specialized equipment.

A preferred method of making the ALC composition of the present invention is now described with reference to FIGS. 1 and 2, which illustrate a system containing two sets of interconnected sterile infusion bags. The system is sealed so that there is no exposure to the outside environment. Specifically, the tubes connecting the two sets are welded together to form one system using a Sterile Connecting Device (e.g., TSCD®-II Cat number ME-203AH of Terumo). More specifically, to ensure compliance with sterility standards, the welding and cutting of the tubes is done by pre-heating special wafers, typically at about 300° C. (although sterility can be effectively achieved by pre-heating at lower or even higher temperatures). This high temperature increases the sterility of the welding procedure. To further ensure sterility, the welding may be performed in a class 100 Biological Safety Cabinet within a class 100,000 containment area.

As illustrated in these figures, the system contains two sterile bag sets. Set 1, containing bags A, B, and C, is a standard, commercially available triple bag set commonly used for blood transfusion. A human blood sample, typically in the volume of about 400 to about 550 ml, is collected in a blood bank via venipuncture and placed into bag A, and then fractionated into its component parts using standard techniques into bags A, B and C. For example, bag A containing the blood sample is centrifuged. After centrifugation, the blood components are separated, e.g., using a blood component extractor manufactured by Baxter. The buffy coat containing leukocytes is placed into bag C, plasma is placed into bag B and erythrocytes remain in bag A. Thus, as a result of this process, bag A contains packed erythrocytes; bag B contains plasma; and bag C contains the buffy coat containing leukocytes (and possibly residual plasma and erythrocytes). Alternatively, the blood components can be separated from whole blood via apheresis techniques known in the art.

Bag A is then disconnected from the three-bag set. As illustrated in FIG. 2, bags B and C are then welded to custom made infusion bags 1-5 (Set-2) to form the system used to make the activated leukocyte composition. As described in these embodiments, bags 1-5 have volumes of 500 ml, 50 ml, 50 ml, 100 ml and 500 ml, respectively. As disclosed above, welding is performed with a sterile connecting device.

Bag 1, which is used for both first and second incubations of the leukocytes, contains 200 ml of sterile filtered air. If bag 1 is gas-permeable, there will be no need for air bags. Gas-permeable bags may also be treated or otherwise modified so that they become adhesive for leukocytes. For example, the bags may contain scaffolds or leukocyte agonists such as complement protein, interferon-alpha, interferon-gamma and interleukin-12. Leukocyte adhesion to the bag surface could be beneficial for their ability to release soluble agonists. The bags could be made from adhesive plastic or regular plastic treated in such a way as to become adhesive (corona discharge, liquid gas plasma, etc.), or coated with extracellular matrix proteins or chemically modified. The scaffolds may be in different shapes and in particular could be microbeads, biodegradable or not biodegradable, e.g., made of collagen (or fragments of collagen, wherein the collagen or collagen fragments are mammalian in origin, such as human or bovine-derived collagen or fragments thereof), or made of PLA, PGA (polylactic acid, polyglycolic acid) or similar synthetic polymers, hydrogel scaffolds made of gelatin, hyaluronic acid alginate or fibrin sealer. Scaffolds could be coated with adhesion receptors, extracellular matrix proteins such as fibronectin or laminin or with active binding peptides from extracellular matrices, such as RGD. Scaffolds or microbeads could be also coated with activating stimuli or stimulating antibodies (the stimuli that otherwise are not desirable in the product will be eliminated together with scaffolds at the end of the production process).

Bag 2 contains a solution (e.g., 20 ml of buffered sodium chloride solution (8.91% NaCl, USP), or any other physiologically acceptable solution containing inorganic ions, organic osmolytes such as sucrose, or some combination thereof, such as Lactated Ringers (Hartmans) solution), which serves to restore the leukocytes to isotonicity following hypo-osmotic shock. When the sodium chloride solution is added to 200 ml of distilled water (in bag 5), it becomes a 0.9% NaCl solution. Bag 3 contains 20 ml of sterile filtered air. Bag 4 contains a solution (e.g., about 60 ml of buffered calcium chloride solution (1.17% $CaCl_2$ dihydrate, USP), which acts to coagulate the plasma in bag B, and to facilitate separation into platelets and serum. Bag 5 contains about 200 ml water.

The set is packed as a single unit and sterilized using high pressure steam, which greatly reduces the risk of secondary infection to the patient.

The leukocytes are then transferred from bag C into bag 1 and incubated while the bag is maintained in a vertical or in a flat position and under activating conditions including time and temperature, to allow them to become activated. For purposes of the present invention, leukocyte activation is defined as a process involving at least one stage, by which the cells (leukocytes) undergo a transition from a quiescent to a functionally active state which is accompanied by synthesis of biologically active substances or translocation of pre-synthesized substances, e.g., cytokines including IL-8, from the cytoplasm to the cellular membrane or their release into extracellular medium (which in this case is serum). Activation of leukocytes in vivo may involve migration of the cells closer to and along the blood vessel wall, which is mediated by P-selectin (and increased CD42b expression), increased adhesion of leukocytes to the endothelial wall, spreading and extravasation, which is mediated to a large degree by activated CD11b that interacts with endothelial ligands ICAM-1 and ICAM-2; migration to the focus of inflammation via interaction with extracellular matrix proteins e.g., laminin) and functional responses to inflammatory stimuli such as respiratory burst, degranulation, phagocytosis and release of cytokines. For purposes of the present invention, activation of the leukocytes, at least as a result of the first incubation, may be indicated by increased expression of activated form of CD11b receptor on leukocyte populations including granulocytes, monocytes and lymphocytes, and higher expression levels of CD69, a lymphocyte-specific activation marker. In some embodiments, leukocytes that have undergone the first incubation may also exhibit increased levels of CD69, a lymphocyte-specific activation marker, express platelet marker 42B (as a result of the interaction between activated granulocytes and monocytes with residual platelets in the buffy coat via p-selectin) and/or increased production of IL-8. Yet other indicia of leukocyte activation may include increased production of one or more of proteins or polypeptides, lipids, sugars, oxygen radicals and other biochemical moieties that function as adhesion molecules, cytokines in addition to IL-8, growth factors, enzymes, transcription factors and cell signaling receptors and mediators. Altered expression levels of any of these molecules is assessed from the standpoint of the leukocytes contained in a "fresh buffy coat" (as described herein), without being subjected to an incubation. Once the leukocytes are activated, they remain activated and as described herein, as a result of subsequent steps in the inventive methods, may achieve higher levels of activation, e.g., even greater expression levels of CD11b; greater or even greater expression levels of CD69, and even lower expression levels of CD62L. Thus, the first and (the optional) second incubation, and the intervening steps, may be collectively referred to as the "activation process".

In some embodiments, the leukocytes are incubated simply by allowing them to stand at room temperature. For purposes of the present invention, room temperature refers to a temperature in the range of about 12° C. to about 28° C., and in some embodiments from about 16° C. to about 25° C., from about 18-25° C. and from about 20-25° C. The time period of incubation, which may vary depending upon the temperature, generally ranges from about 30 minutes to about 24 hours. The incubation time needed to activate the leukocytes will be roughly inversely proportional to the temperature at which the incubation is conducted. Thus, incubation times will be lower at increased temperatures. For example, in embodiments where leukocytes are allowed to stand at room temperature, the incubation time generally ranges from about 90 minutes, and upwards of 2, 3, 4, 5, 6, 7, 8, 9, 10, 11, 12, 13, 14, 15, 16, 17, 18, 19, 20, 21, 22, 23 or upwards of 24 hours (and subranges thereof which include, for example a minimum time of anywhere from 90 minutes, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs or higher). In preferred embodiments, the incubation time at room temperature ranges from about 3, 4, 5, 6, 7 or 8 hours to about 20 hours. In a more preferred embodiment, incubation of the leukocytes occurs at about 18° C. to about 24° C. for about 8 hours to about 12 hours. In other embodiments, incubation of the leukocytes involves exposing them to heat, e.g., at a temperature above room temperature and up to about 37° C. The time period for incubation at elevated temperatures generally ranges anywhere from 30, 45, 60, or 90 min to about 2, 3, 4, 5, 6, 7, 8, 9, 10, 11 or 12 hours (and even upwards, in hour increments to about 24 hours (and subranges thereof which include, for example, a minimum time of anywhere from 30, 45, 60 or 90 mins, 2 hrs, 3 hrs, 4 hrs, 5 hrs, 6, hrs, etc.).

After incubation, the leukocyte suspension (including any cells that adhere to the bag during the first incubation which will immediately detach after addition of water) is subjected to hypo-osmotic shock. In preferred embodiments, hypo-osmotic shock is performed immediately (i.e., upon completion of the preceding step without any intervening step or unnecessary delay, typically less than 2 minutes). The hypo-osmotic shock may be initiated by transferring the distilled water from bag 5 to bag 1 containing the leukocytes. The hypo-osmotic shock treatment is typically conducted for about 25-45 seconds. Lesser times within this range are preferred, as it is believed that fewer CD4+ T cells are lost. CD4+ T cells are known to produce various cytokines (e.g., IFN gamma, IL-2, IL-4 IL-17), which might be beneficial for wound healing. Following this step, and preferably immediately thereafter, isotonicity is restored to the leukocytes by transferring the sodium chloride solution from bag 2 to bag 1.

The ratio of the volume of sodium chloride solution to cell suspension in water is generally about 1:10.

Following the treatment that restores isotonicity, the entire 7-bag system (now containing only 5 bags) is centrifuged. This process removes water and salt solution added in the course of the two prior steps, and prevents exposure of the leukocytes to hemolysate (of the erythrocytes). As a result of the centrifugation, the leukocytes form a pellet. After centrifugation, the supernatant from bag 1 is transferred into bag C, and the leukocyte pellet formed in bag 1 as a result of the centrifugation is re-suspended in serum. As described above, this composition may be used therapeutically in the inventive methods.

The preferred embodiment involves at least one additional step. Thus, in a separate step, which may be conducted concurrently with the leukocyte incubation, plasma is separated into platelets and serum by the use of a coagulant such as $CaCl_2$. This process results in formation of a blood clot of predominately fibrin strands and platelet aggregates. The blood clot is separated from serum, which is essential plasma depleted of clotting proteins and most of the platelets. As a result of this treatment, the resulting serum has a residual platelet level that generally ranges from about 0 to about $0.2 \times 10^3$ per µL Thus, in this representative embodiment, $CaCl_2$ from bag 4 is transferred to bag B. Bag B, which now contains a composition of plasma and $CaCl_2$, is typically allowed to coagulate at a temperature of about 37° C. The plasma remains in contact with the coagulating agent for substantially the same period of time the leukocytes are incubated. In this preferred embodiment of the present invention, the activated leukocytes are then incubated in the coagulated plasma before the final composition is made. Generally, this second incubation period is conducted for about 1-2 hours at 37° C.

It should be noted that although the plasma and the serum for use in various aspects of the invention may be prepared at the same time as the activated leukocyte composition (whether from the same or a different blood sample), in alternate embodiments the serum and/or plasma is prepared independently of the activated leukocyte composition. For example, serum and/or plasma may be obtained from a commercial or non-profit supplier of blood products. The serum and/or plasma may be recently obtained from one or more donors, or it may have been stored for a period of time, and may be stored frozen. Further, since the blood samples used to prepare the serum and/or plasma need not be the same as used to prepare the activated leukocytes (whether or not they are from the same donor), their preparation need not occur at the same physical location or at the same time as preparation of the activate leukocyte composition.

Figure 2A:
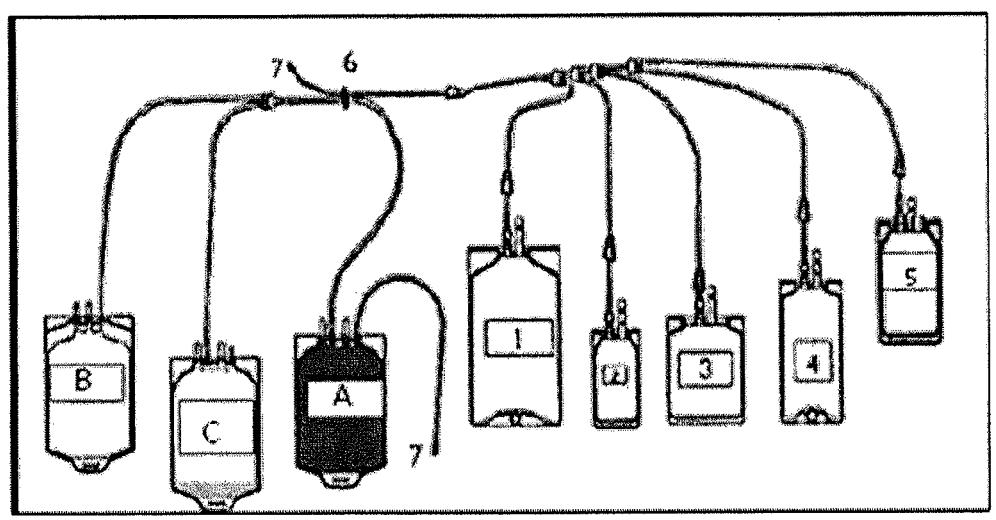
FIG. 2A schematically depicts a second portion of the representative system for producing ALC compositions of the present invention, which includes a 7-bag set after bag A with RBC is removed from the system and bags B and C from FIG. 1 are welded to bags 1-5 (Set-2)
Figure 2B:
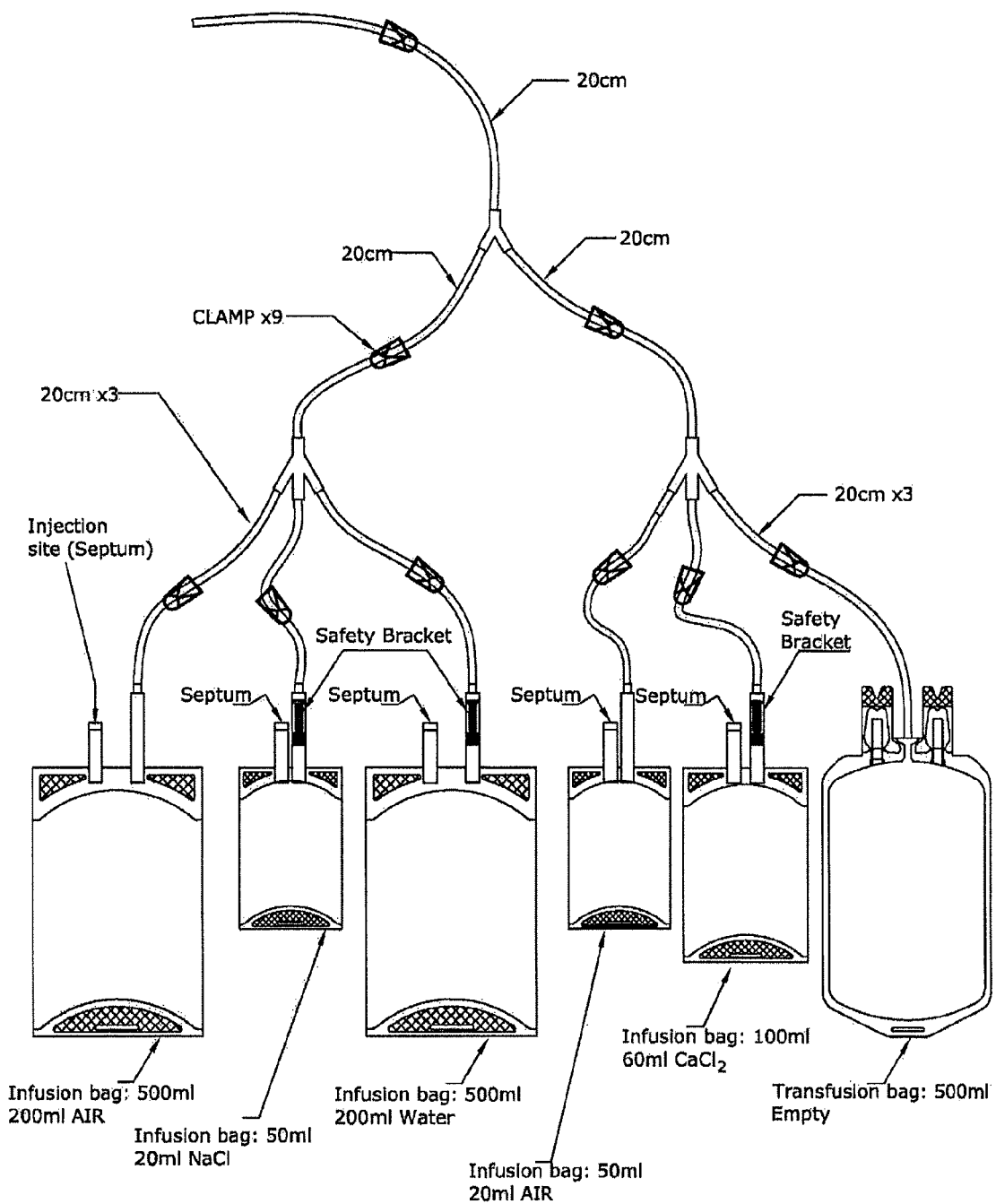
FIG. 2B shows a 6-bag set that may be used in lieu of bags 1-5 in FIG. 2A.

In an alternative and even more preferred embodiment, the 6-bag set illustrated in FIG. 2B may be used in place of bags 1-5 illustrated in FIG. 2A. The additional bag helps maintain sterility of the clean room production site. In this embodiment of the present method, after separation into buffy coat, plasma and RBC, leukocytes as previously described are transferred from bag C to a sterile bag 1 and the plasma is placed into the sixth bag which is also sterile, and then the 6 bag system is separated from the original triple bag set.

In other embodiments, the ALC composition may be prepared from smaller volumes of blood samples, with commensurate decreases in volumes of all solutions and use of smaller bags. Furthermore, use of these different size bags yield ALCs with different compositions. Even in these embodiments, allogeneic or autologous blood samples may be used as starting materials. Use of smaller volumes provides the clinician with the ability to perform the blood collection autonomously, without using an external blood bank, such as in emergency situations in treating patients with otherwise healthy immune systems but suffering from some type of traumatic wound (e.g., battlefield and combat conditions). In these embodiments, testing for transmittable diseases and antigens may be dispensed with. However in such cases, patients with refractory wounds are not clinically acceptable blood donors for effective ALC preparation. When this situation arises, ALC will be produced from allogeneic donors by the means described herein.

The ALCs of the present invention include leukocytes, e.g., granulocytes, monocytes and lymphocytes. Granulocytes include neutrophils, eosinophils and basophils. In its broadest sense, the leukocyte population of the ALC generally contains about 40% to about 90% granulocytes, about 5% to about 20% monocytes and about 5% to about 30% lymphocytes. Specific amounts of the cells may differ based on the analysis techniques employed. When analysis is performed using FACS (e.g., using a side-scatter versus a forward-scatter dot plot analysis), the leukocyte composition generally contains about 55% to about 80% granulocytes; about 5% to about 15% monocytes and about 5% to about 30% lymphocytes, and in some embodiments, comprises about 58-76% granulocytes; about 5-11% monocytes and about 9-23% lymphocytes. When analysis is performed using a Cell Dyn Analyzer, the leukocyte composition generally contains about 50% to about 90% granulocytes; about 5% to about 15% monocytes; and about 10% to about 25% lymphocytes. The subpopulation of lymphocytes in the ALC may confirm the following cells in the general ranges as follows: about 7% to about 25% B cells (CD19+); about 20% to about 30% NK cells (CD3−/CD56+), about 40% to about 60% T cells (CD3+); about 0.1% to about 30% of NKT cells CD3+/CD56+, about 8% to about 20% of T helper cells (CD4+/CD3+), and about 20% to about 30% of CD8+/CD3+ cells. In preferred embodiments, the lymphocyte subpopulation is enriched with at least 9% CD56+ cells (CD3−/CD56+; CD3+/CD56+; CD3+/CD56+/CD8+), the amount of the T helper lymphocytes (CD4+/CD3+) is decreased to less than 20%, and/or the ratio of T-helper to T-suppressor cells (CD4+/CD3+: CD8+/CD3+) is less than 0.8. The ALC of the present invention may also include stem and progenitor cell populations. For example, the ALC may further contain mesenchymal stem cells and endothelial progenitor cells, each in amounts ranging from about 0.1% to about 5.0% of the total cell population in the ALC.

In one embodiment, the ALC has a shelf life (i.e., can be stored prior to use) ranging up to 72 hours following production, for example about 5, 10, 15, 20, 21, 22, 23, 24, 25, 26, 27, 28, 29, 30 or more hours following its production.

In one embodiment, the ALC has a shelf life extends up to 97 hours following collection of the blood sample or blood samples used to prepare the ALC, that is about 5, 10, 15, 20, 25, 30, 35, 40, 45, 50, 55 or more hours following collection of the blood sample or blood samples used to prepare the ALC.

Patients suffering from wounds can be physiologically compromised or otherwise healthy. For example, due to already impaired metabolic systems, diabetics and other medically compromised patients are candidates for ALC derived from heterologous blood, as their own leukocytes may not be optimal for the procedure. However, otherwise healthy patients, as in the example of trauma patients, are also good candidates for ALC compositions of the present invention.

The present invention is useful in promoting healing in a multitude of wound types. Although in practice it may be used in combination with other treatment modalities, it does not require them to achieve effective wound healing. The inventors have contemplated application of the ALC to any type of wound and foresee no limitations as to the type of wound that can be treated. The ease of application, e.g., with a standard syringe or similar application device, makes the inventive ALC compositions safe and easy to use.

Wounds amenable to treatment with the invention are typically in the faun of burns, punctures, and cuts or tears of the living tissues. Wounds of the skin can penetrate the epidermis, dermis or in the case of full-thickness wounds, the subcutaneous tissue. Thus, representative types of wounds amenable to treatment with the compositions and methods of the present invention include burns (e.g., caused by exposure to fire or an agent that is highly caustic to skin such as radiation), ulcers (e.g., decubital or pressure ulcers; venous ulcers and diabetic ulcers), deep sternal wounds, e.g., following open heart surgery (to the great saphenous vein after coronary revascularization and harvesting of the great saphenous vein); and post-operative wounds following abdominal, orthopedic and any other types of surgery. Other wounds are those which result from trauma such as incurred during combat or other violent activity, including wounds caused by gun shots, knives, or any other object able to cause a cut or tear in the skin. Wounds of the oral cavity (e.g., teeth), as well as wounds that arise as a side-effect of medication or as a symptom of various pathologies (e.g., sores associated with Kaposi's Sarcoma), as well as internal wounds (e.g., ruptures of muscle tissue such as anal fissures), and wounds or lesions to the gastrointestinal tract, such as ulcers in the stomach or intestines) may also be amenable to treatment with the present invention. In addition to providing a wound-healing effect, the ALC of the present invention may also provide a benefit of inhibiting onset of infection following such therapy, particularly in the context of surgery.

The ALC of the present invention may also be useful to remove tattoos. Without intending to be bound by theory, it is believed that the activated granulocytes and neutrophils engulf and degrade the ink.

The ALC may also be used to treat any wounds exacerbated by vascular insufficiency. Vascular insufficiency, for purposes of the present invention, refers to inadequate blood circulation resulting in insufficient perfusion to the afflicted areas. Such insufficiency can be caused by trauma (e.g., damage to the vasculature adjacent to a skeletal fracture), or various pathologies (e.g., diabetes and atherosclerosis). In either instance, whether trauma or disease induced, vascular insufficiency decreases the likelihood of effective wound healing. The ALC may be useful in improving wound healing outcomes in these patients and should be administered according to the methods described herein. Additionally, treatment algorithms should not be limited by the severity or type of wound, or the extent of vascular insufficiency. ALC may be more efficacious in patients presenting with the most severe wounds and vascular insufficiency.

In general, application of the activated leukocyte composition is accomplished by means of one or more injections of the ALC at a single or multiple sites, using a suitable syringe (e.g., a 2 ml syringe fitted with an 18 G or 25 G needle) directly into the wound or the tissue surrounding the wound. In some embodiments, injection occurs about every one centimeter to about every three centimeters for the entire length of the wound. At each injection site, about 0.1 to about 0.3 ml of ALC is injected. ALC compositions of the present invention contain leukocytes in a concentration that generally ranges from about $2 \times 10^6$ cells/ml to about $4 \times 10^6$ cells/ml.

For injection into the wound, it is preferred to use a Luer-Lock syringe or any other commercially available syringe that has a locking mechanism between the syringe and the needle. The biological space of a wound, particularly a pressure wound, is often limited. When injecting into a wound, there is a risk of pressure causing the syringe to separate from the needle. Using a locking syringe eliminates this risk.

When injection into the wound tissue is not possible, the ALC can be applied directly into the cavity of the wound. Application in this method can be done using direct application with a syringe or tubing.

The ALC may be applied to or around the wound site with the aid of a dressing. Dry dressings include gauze and bandages, non-adhesive meshes, membranes and foils, foams, and tissue adhesives. Moisture-keeping barrier dressings include pastes, creams and ointments, nonpermeable or semipermeable membranes or foils, hydrocolloids, hydrogels, and combination products. Bioactive dressings include antimicrobial dressings, interactive dressings, single-component biologic dressings, and combination products (e.g., ointments, gels, fibrin sealant, growth and angiogenic factors (e.g., PDGF, BEGF, collagen)). In some embodiments, the wound is packed with sterile gauze soaked in the ALC. The dressing, such as sterile gauze pads, may be saturated with compositions such as Lactated Ringer (Hartman) Solution, alginate containing dressing, polyurethane dressing or carboxymethylcellulose dressing, which is applied to cover the wound, followed by application of dry dressing. If the subject wound is highly infected, then silver dressings such as Silverlon can be applied. The choice of post-injection dressing is based on the determination of the clinician. Commercial availability, history of past clinical success, and patient tolerance are all factors to be considered in the selection of a wound dressing. The dressing may be removed periodically, e.g., typically after about 24 hours, in order to irrigate the wound e.g., with sterile water and soap.

In another embodiment, the ALC composition is combined with a physiologically inert and/or resorbable matrix or scaffold prior to administration. The matrix or scaffold may be formed from any material suitable for implantation into a person. For example, the matrix or scaffold may comprise any biocompatible material including collagen, hyaluronic acid, or gelatin, or combinations thereof. The collagen may be obtained from any source, including collagen prepared from human tissue or the tissue of other collagen-producing mammals. The combination of the ALC composition and matrix/scaffold material may form a gel or putty that is administered to a person by means of a press fit, or by injection. This allows for a sustained delivery of the ALC into the site which benefits the patient in that the cells have a longer period in situ. In some embodiments, the mixture of the ALC composition and matrix/scaffold material is prepared commercially and provided to a health-care provider pre-mixed. In other embodiments, the health care provider mixes the ALC composition and the matric/scaffold prior to administration to a person.

The ALC compositions may be applied to the wound once or more than once, e.g., after 4 weeks, once a clinician determines whether another application is necessary. Factors that may be taken into account include increased wound dimensions (width, length and depth), suppuration, pyrexia or any other sign or symptom indicating a recalcitrant infection such that re-treatment is warranted. In addition to re-treatment, referral for surgical debridement may be indicated at any point the clinician deems appropriate.

The ALC may be used in conjunction with any other conventional wound treatment, such as negative pressure, warming (therapeutic heat), electrical stimulation, magnetism, laser phototherapy, cycloidal vibration therapy and ultrasound. It also can be used with biological therapy such as larva therapy, skin substitutes, cultured keratinocytes (Epicel, Genzyme biosurgery), human dermal replacement (Dermagraft, Smith and Nephew Inc.), cadaver derived processed dermis (Allodeim, Life Cell Corporation), Bilayered Skin Equivalent (Apligraf, Organogenesis Inc.), TransCyte (Smith and Nephew Inc.), Growth Factors (PDGF is currently the only growth factor licensed for topical use), and fibrin sealant. In some embodiments, the ALC is used in conjunction with negative pressure wound therapy (NPWT) (one example being the V.A.C., which is a commercially available wound therapy manufactured by KCI). Negative pressure therapy promotes wound healing by applying negative pressure to a wound. In these embodiments, ALC is preferably applied to a wound prior to negative pressure therapy. In yet other embodiments, the ALC is used in conjunction with hyperbaric oxygen therapy (Thackham, 2008) or ozone therapy. For example, the ALC can be applied to a wound just prior to a patient receiving hyperbaric therapy. The ALC may also be used in conjunction with low-energy shock wave therapy (e.g., impulses of about 0.1 mJ/mm$^2$; 5 Hz) per centimeter of wound length). See, e.g., Dumfarth, et al., Ann. Thorac. Surg. 86:1909-13 (2008).

After treatment, the wounds may be evaluated for length, width and height measurements. Typically, a wound is considered healed when all measurements of these parameters are negligible. The ALC may also provide an analgesic effect.

The activated leukocyte composition is particularly useful in wounds including diabetic foot ulcers and decubital ulcers. Decubital ulcers are pressure ulcers caused by impeded blood flow, usually due to prolonged pressure on a particular area. (Berlowitz, 2007) Decubital ulcers cause morbidity and mortality in elderly people. At least 48% of stage 1V pressure ulcers remain unhealed after one year of treatment. (Girouard, 2008). Patients suffering from decubiti also commonly have co-morbid pathologies such as diabetes and hypertension. These pathologies further complicate the successful treatment of decubiti.

In one embodiment for treating decubital ulcers, the composition is aspirated into a sterile syringe of any size, using an 18-gauge (18G) needle. Aspiration is performed slowly to minimize damage to the cells. While the size of the syringe and needle are by no means limiting, a large gauge needle is preferred for aspiration. This facilitates the transfer and reduces cell damage.

Application of the activated leukocyte composition to the ulcer comprises injecting the composition into the wound. The entire sample in the syringe can be deployed and the clinician can choose to administer additional ALC if it is determined to be necessary based on clinical parameters.

The 18G needle used for aspiration is exchanged with a needle ranging in size from 22-35 G. The ALC may be injected into the wound in various locations. In one embodiment, injection occurs about every one centimeter to about every three centimeters for the entire length of the wound. At each injection site, 0.1-0.3 ml of ALC is injected.

In another embodiment, the entire syringe can be injected at one time into a single site within the wound.

Aspect(s) of the present invention will now be described in accordance with the following non-limiting examples.

EXAMPLE 1

Analysis of Cellular Activation

An activated leukocyte composition made in accordance with the preferred embodiment of the present invention was quantified by the analysis of various cell surface markers. An increase in platelet interaction with either monocytes or granulocytes through the expression of P selectin is a sign of activation of the monocytes and granulocytes. Because residual platelets remaining in the buffy coat adhere to activated granulocytes and monocytes the latter exhibit platelet marker CD42b on their surface.

CD62L is an adhesion receptor from a selectin family. It is constitutively expressed on all classes of leukocytes including granulocytes, monocytes and lymphocytes. Upon activation, leukocytes rapidly shed off CD62L from their surface. CD62L is a plasma membrane protein which is shed during activation and thus decreases with cell activation. CD42b is a platelet activation marker involved in the process of coagulation as an aggregating factor. It interacts with extra-cellular matrix as well as with adhesion molecules and also used in the present invention as an indicator of monocyte and granulocyte activation.

Leukocytes were sampled at three time points: immediately prior to the beginning of the production process (fresh buffy coat (FBC)); right after the first incubation (incubated buffy coat (IBC)); and from final activated leukocyte composition or final product (FP), meaning after hypo-osmotic shock, followed by 90 min incubation with serum at 37° C. At each time point, leukocytes were labeled with specific monoclonal antibodies against corresponding activation markers and then analyzed by flow cytometry.

For antibody staining, cells from each time point were washed with FACS staining solution (PBS, 2% Normal Mouse Serum; 0.02% Sodium Azide), aliquoted at $0.5 \times 10^6$/tube and incubated with appropriate monoclonal antibodies for 30 min in the dark. After incubation, the cells were treated with erythrocyte lysis buffer, washed, re-susupended in PBS and analyzed on FACSCalibur flow cytometer (Becton Dickinson). In order to better distinguish between leukocyte populations, cells labeled with CD62L or CD42b were also double-labeled with the antibody against a monocyte marker CD14 conjugated to allophycocyanin (APC). Cells stained with irrelevant but isotype-matching antibodies (together with anti-CD 14 antibodies) under the same conditions were used as negative controls For CD62L positive (+) staining cell suspension was incubated with anti-human CD14 (APC) and anti-human CD62L (FITC) antibodies at +4° C. For CD42b+ staining cell suspension was incubated with anti-human-CD14 (APC) and anti-human CD42b (PE) at RT. Monocytes were determined as CD14 brightly positive cells and granulocytes were identified as CD14 dim positive cells with high side light scattering properties (SSC). The results of the first experiment are summarized in Table 1, while Table 2 presents average results for two experiments. The data in the Tables describe percentage of leukocytes (granulocytes and monocytes) positive for each marker in compositions sampled at three time points (FBC, IBC and FP). The CD62L or CD42b positive cells were defined as granulocytes and monocytes with fluorescence greater than that of the same cells incubated with an appropriate isotype-matching control antibody.

TABLE 1

Expression of cell surface markers indicating leukocyte activation (representative batch)

| | FBC | IBC | FP |
|---|---|---|---|
| % of CD62L positive cells | | | |
| Monocytes | 68 | 55 | 44 |
| Granulocytes | 97 | 47 | 39 |

TABLE 1-continued

Expression of cell surface markers indicating leukocyte activation (representative batch)

|  | FBC | IBC | FP |
|---|---|---|---|
| % of CD42b positive cells | | | |
| Monocytes | 26 | 74 | 92 |
| Granulocytes | 3 | 15 | 39 |

TABLE 2

Average expression of cell surface markers indicating leukocyte activation

|  | FBC | IBC | FP |
|---|---|---|---|
| % of CD62L positive cells | | | |
| Monocytes | 64.98 | 54.77 | 38.285 |
| Granulocytes | 97.13 | 62.44 | 55.645 |
| % of CD42b positive cells | | | |
| Monocytes | 40.4 | 68.5 | 93.0 |
| Granulocytes | 3.1 | 8.8 | 49.7 |

As a result of variability between the batches, which depends on individual characteristics of blood donors, the average of two tests (Table 2) was different from the individual results (Table 1), however both tests and the average data demonstrated similar patterns of expression of CD62L and CD42b on monocytes and granulocytes. In the raw material (fresh buffy coat; FBC) percentage of cells expressing CD62L was the highest. It decreased during the first incubation (incubated buffy coat; IBC) as a result of cell activation and shedding off of CD62L. Further leukocyte activation during the rest of the production process caused additional loss of CD62L from the cell surface, which resulted in the lowest percentage of CD62L-positive monocytes and granulocytes in the final product (FP).

Expression of CD42b had the opposite pattern. The percentage of CD42b-positive monocytes and granulocytes was lowest in FBC, however it increased in the IBC because leukocytes became activated and interacted with platelets membranes containing CD42b. Leukocyte activation continued during the rest of the production process resulting in the highest percentage of CD42b-positive monocytes and granulocytes in the FP.

Thus, as shown in FIGS. 3A and 3B and Tables 1 and 2, comparison of CD42b and CD62L expression at different stages of the production process demonstrated increase of the percentage of CD42b and decrease of CD62L-positive granulocytes and monocytes already at the stage of Incubated Buffy Coat (IBC) with further respective increase and decrease in the final product (FP), which was in accordance with their activated state.

EXAMPLE 2

Analysis of an Activated Leukocyte Composition

Tables 3 and 4 depict the cellular compositions of the final ALC harvested at the end of production as determined by analysis with a Cell Dyn analyzer. Cells were analyzed (after activated leukocytes were re-suspending suspended the activated leukocytes in serum) was analyzed in triplicate with an automatic Cell Dyn analyzer. In addition cell viability was confirmed by Viable cells were stained using trypan blue exclusion and observed under a microscope. Tables 3 and 4 summarize the cellular composition of 8 batches of the final ALC.

TABLE 3

Composition of Activated Leukocyte Composition

|  | Platelets ($10^3/\mu l$) | Erythrocytes ($10^6/\mu l$) | Leukocytes ($10^3/\mu l$) |
|---|---|---|---|
| Concentration in final ALC | 46.8 | 0.1 | 6.8 |
| Standard Deviation | 39.2 | 0.06 | 3.8 |

TABLE 4

Leukocyte Composition in ALC
Leukocytes

|  | Granulocytes | | | Monocytes % | Lymphocytes % |
|---|---|---|---|---|---|
|  | Neutrophils % | Basophils % | Eosinophils % | | |
| % in final ALC | 65.5 | 1.6 | 4.6 | 9.1 | 18.5 |
| Standard Deviation | 8.2 | 0.3 | 3 | 2.1 | 4.1 |
| Range | 52-78 | 1-2 | 1-9 | 6-12 | 13-24 |

EXAMPLE 3

Analysis of an Activated Leukocyte Composition

Leukocytes were sampled at three time points: immediately prior to the beginning of the production process (fresh buffy coat (FBC); right after the first incubation (incubated buffy coat (IBC)); and at the end of the process thus producing the final product (FP), meaning after hypo-osmotic shock, followed by a second, 90 min incubation with serum at 37° C. At each time point, leukocytes were labeled with specific monoclonal antibodies against corresponding activation markers and then analyzed by flow cytometry.

For antibody staining, cells from each time point were washed with FACS staining solution (PBS, 2% Normal Mouse Serum; 0.02% Sodium Azide), aliquoted at $0.5 \times 10^{6/0}$ and incubated with appropriate monoclonal antibodies for 30 min. at +4° C. in the dark. After incubation, the cells were treated with erythrocyte lysis buffer, washed, re-suspended in PBS and analyzed on FACSCalibur flow cytometer (Becton Dickinson). Anti-CD11b and anti-CD62L antibodies were conjugated to phycoerythrin (PE), and CD69 antibody was conjugated to fluorescein isothiocyanate (FITC). In order to better distinguish between leukocyte populations, cells labeled with CD11b were also double-labeled with the antibody against a monocyte marker CD14 conjugated to allophycocyanin (APC), and cells labeled with and CD62L antibodies were also double-labeled with granulocyte marker CD15-APC. In order to identify T and B lymphocytes, cells stained with CD69 antibody were also double-stained with anti-CD3–APC and anti-CD19-APC antibodies. Cells stained with irrelevant but isotype-matching antibodies (together with anti-CD14 or anti-CD15, or anti-CD3/CD19 antibodies) under the same conditions were used as negative controls. Monocytes were determined as CD14 brightly positive cells and granulocytes were identified as CD14 dim positive cells or CD15 bright positive cells with high side light scattering properties (SSC). T Lymphocytes were determined as CD3 positive cells and B lymphocytes were determined as CD19 positive cells. The results of 4-6 such individual experiments are summarized in Tables 5, 6 and 7. The data are presented as Mean Fluorescence Intensity of stained cells plus/minus StDev.

The data shown in Table 5 demonstrate that the level of expression of CD11b recognized by both general (D12) and anti-activated form (CBRM⅕) antibodies significantly increased at the end of the process (FP) on all leukocyte populations compared to Fresh Buffy Coat (FBC). Up-regulation of activated form of CD11b was more pronounced.

the stage of Incubated Buffy Coat (IBC). At the end of the process (FP), CD62L levels were negligible (Table 6).

As shown in Table 7, the upregulation of CD11b and down-regulation of CD62L were consistent with the expression of a specific lymphocyte activation marker CD69, which increased from practically no expression to moderate but significant levels.

EXAMPLE 4

Analysis of secretion of IL-8 Cytokine by Activated Cells During Incubation With Serum An activated leukocyte composition containing $10 \times 10^6$ cells was incubated with 5 ml of serum in accordance with a preferred embodiment of the present invention, and the concentration of IL-8 cytokine was measured at various time points of incubation using optimized ELISA plates from eBioscience. Concentrations of IL-8 (pg/ml) in serum without leukocytes were measured in parallel and subtracted from IL-8 values produced in the presence of activated leukocytes. The results of five experiments are summarized as Mean±SD in Table 8.

TABLE 5

Expression of CD11b on leukocyte populations indicating leukocyte activation.

| | CD 11b (D12 antibody) Mean Fluorescence | | | | CD 11b activated form (CBRM 1/15 antibody) Mean Fluorescence | | | |
|---|---|---|---|---|---|---|---|---|
| samples | GR | Mono | T cells | B cells | GR | Mono | T cells | B cells |
| FBC | 635 ± 282 | 657 ± 104 | 1.6 ± 1.1 | 6.7 ± 3.3 | 22 ± 13 | 6 ± 4 | 0 | 0.2 ± 0.1 |
| IBC | 1099 ± 85 | 589 ± 12 | 1.6 ± 1.2 | 8.6 ± 5.8 | 37 ± 6 | 4 ± 1 | 0 ± 0.1 | 0.3 ± 0.2 |
| FP | 1100 ± 144 | 663 ± 48 | 26.9 ± 21.6 | 14.3 ± 2.2 | 225 ± 85 | 22 ± 8 | 0.6 ± 0.3 | 1.5 ± 0.7 |

TABLE 6

Expression of CD62L on leukocyte populations indicating leukocyte activation.

| | CD 62L Mean Fluorescence | | | |
|---|---|---|---|---|
| samples | GR | Mono | T cells | B cells |
| FBC | 583 ± 428 | 205 ± 187 | 256 ± 123 | 577 ± 165 |
| IBC | 34 ± 25 | 14 ± 8 | 86 ± 54 | 32 ± 19 |
| FP | 19 ± 10 | 16 ± 4 | 13 ± 6 | 24 ± 13 |

TABLE 7

Expression of CD69 on T and B lymphocytes indicating their activation.

| | CD69 Mean Fluorescence | |
|---|---|---|
| samples | T cells | B cells |
| FBC | 0.2 + 0.2 | 0.2 + 0.1 |
| IBC | 0.6 + 0.4 | 0.6 + 0.4 |
| FP | 6.3 + 4.5 | 8.2 + 3.4 |

Comparison of CD62L expression at different stages of the production process demonstrated that it drastically and significantly decreased on all leukocyte populations already at

TABLE 8

Concentrations of IL-8 (pg/ml) released into serum by activated leukocytes.

| Time of incubation of ALC with serum | | |
|---|---|---|
| 0.5 hour | 1 hour | 5 hours |
| 1115 ± 519 | 2581 ± 865 | 12461 ± 9491 |

The data presented in Table 8 demonstrate sustained release of IL-8 into serum by ALC for at least 5 hours.

EXAMPLE 5

Identification of Mesenchymal Stem Cells in ALS

ALS was sampled at the end of the production process, doubled-labeled with specific monoclonal antibodies against pan-leukocyte marker CD45 and MSC marker CD105, and then analyzed by flow cytometry.

For antibody staining, cells were washed with FACS staining solution [2% BSA (Sigma), 2% human blocking serum (Chemicon) in DMEM without phenol red (Sigma), pH=7.4] and aliquoted at 100,000 per 100 microL FACS buffer onto a polypropylene U shaped 96 well plate. Each cell aliquot was incubated with saturating concentrations of antibodies on ice for 30 min. At the end of incubation the plate was centrifuged at 200×g for 3 min, inverted onto a paper towel to drain the supernatant. The cells were washed twice in 200 microL FACS buffer and transferred into polypropylene FACS test tube containing 0.5 ml FACS buffer. The samples were kept on ice and in the dark until running on FACSAria (BD). Anti-CD45 antibody was conjugated to Peridinin Chlorophyll Protein Complex (PerCP) and anti-CD105 antibody was conjugated to fluorescein isothiocyanate (FITC). The following strategy was used to identify MSC on dot plots. First cells with low side scatter were gated on forward scatter (FSC-cell size) vs side scatter (SSC-cell granularity) dot plots (FIG. 4A). Then gated cells with low SSC (practically all cells except granulocytes) were plotted against CD105-FITC fluorescence, and CD105$^{high}$ cells were gated (FIG. 4B). Next CD105$^{High}$ cells were plotted against CD45-PerCP fluorescence, and CD45 negative cells were gated (FIG. 4C). When these cells are plotted in FSC vs SSC coordinates, a quite homogeneous population in terms of size and surface properties emerges (FIG. 4D). Statistical analysis of the population of CD45 negative/CD105 highly positive cells showed that these cells compose 0.2% of all cells in ALS and 2.7% of CD 105 highly positive cells (FIG. 4E).

EXAMPLE 6

Identification of Endothelial Progenitor Cells in ALS

ALS was sampled at the end of the production process, doubled-labeled with specific monoclonal antibodies against CD31, a marker of endothelial cells and against vascular endothelial growth factor receptor 2 (VEGFR2, also known as KDR), a marker of early endothelial progenitors, and then analyzed by flow cytometry.

Figure 5B:
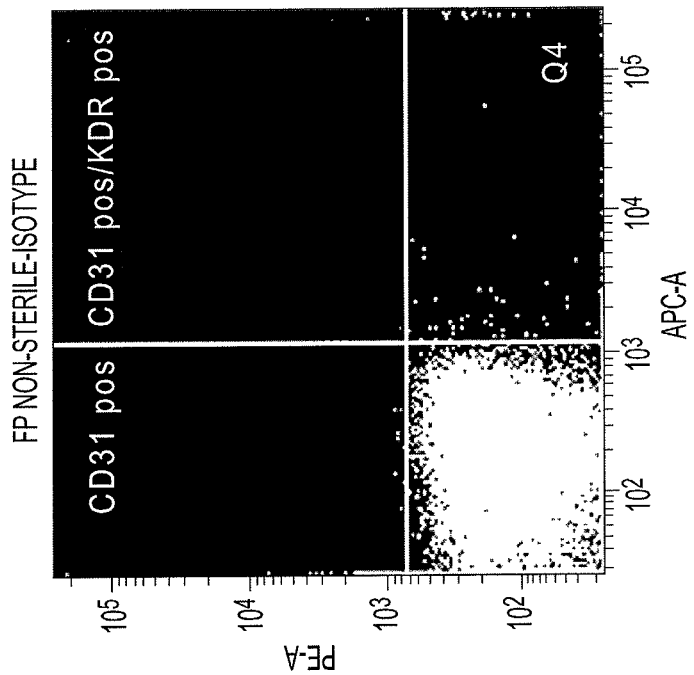
FIGS. 5A and 5B demonstrate the results of identification of endothelial progenitor cells in ALS using flow cytometry analysis. A dot plot graph depicted on FIG. 5A, shows distribution of ALS cells stained with antibodies against two markers of endothelial progenitors, CD31 and KDR, according corresponding fluorescences. The upper right quadrant of the dot plot contains cells double-positive for both markers. Statistical analysis showed that this $CD31^{positive}_{/KDR}{}^{positive}$ cell population composes 0.2% of all cells in ALS.
Figure 5A:
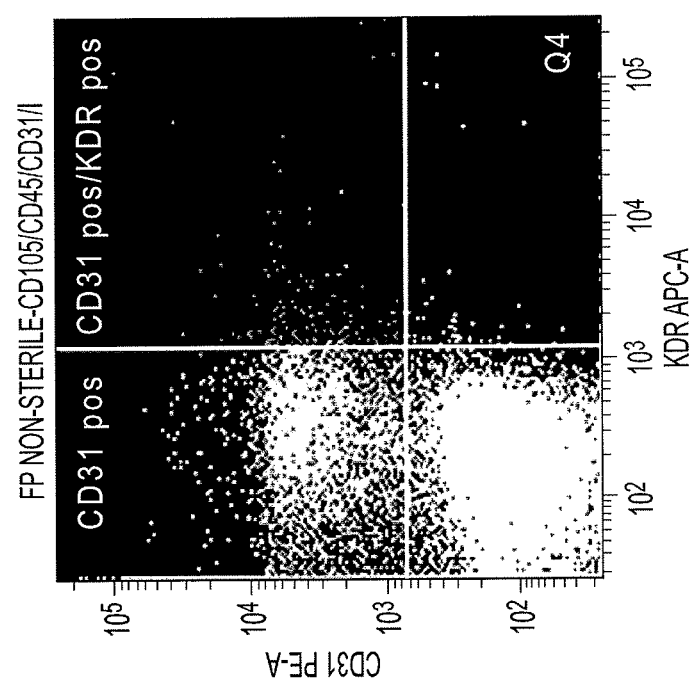

For antibody staining, cells were washed with FACS staining solution [2% BSA (Sigma), 2% human blocking serum (Chemicon) in DMEM without phenol red (Sigma), pH=7.4] and aliquoted at 100,000 per 100 microL FACS buffer onto a polypropylene U shaped 96 well plate. Each cell aliquot was incubated with saturating concentrations of antibodies on ice for 30 min. At the end of incubation the plate was centrifuged at 200×g for 3 min, inverted onto a paper towel to drain the supernatant. The cells were washed twice in 200 microL FACS buffer and transferred into polypropylene FACS test tube containing 0.5 ml FACS buffer. The samples were kept on ice and in the dark until running on FACSAria (BD). Anti-CD31 antibody was conjugated to phycoerythrin (PE) and anti-KDR antibody was conjugated to allophycocyanin (APC). The results of flow cytometry analysis are shown in FIG. 5. A dot plot graph is depicted on FIG. 5A, showing distribution of stained cells according to their CD31-PE and KDR-APC fluorescences. The upper right quadrant of the dot plot contains cells double-positive for both markers. Statistical analysis showed that this CD31$^{positive}$/KDR$^{positive}$ cell population composes 0.2% of all cells in ALS. In control experiment an ALS sample was stained with irrelevant but isotype-matched antibodies. No positively-stained cells were found (FIG. 5B).

EXAMPLE 7

Comparison Between Inventive Method and Prior Art Process

To highlight the various unexpected advantages associated with the present invention, embodiments thereof were compared to the process disclosed in U.S. Pat. No. 6,146,890, to Danon ("Danon").

Inventive Embodiments

For purposes of this example, reference is made to FIGS. 1 and 2 illustrated in Applicants' commonly owned International Patent Application No. PCT/IL2010/000882, filed Mar. 10, 2010 (the disclosure of which is incorporated herein by reference), and the preferred procedure disclosed therein with respect to use of the 7-bag system illustrated in those figures. Immediately after separating whole blood into its primary components, i.e., red blood cells, plasma, and Buffy coat, the Buffy coat was transferred from Bag C to Bag 4 and incubated for 12 hours±2 hours at room temperature. This step was followed by transferring the distilled water from Bag 1 to Bag 4 (or bag 5), for purposes of conducting hypo-osmotic shock treatment (resulting in the production of a hemolysate). This treatment was conducted for approximately 45 seconds. Immediately thereafter, the buffered sodium chloride solution contained in Bag 2 was transferred to Bag 4 (or bag 5) for purposes of restoring isotonicity to the Buffy coat (leukocytes).

Contemporaneous with the incubation of the Buffy coat, above, the buffered calcium chloride solution in Bag 3 was transferred to Bag B containing the plasma portion, for purposes of allowing for coagulation of the plasma. This was allowed to take place over the course of 12 hours±2 hours, plus the additional short time during which the leukocytes were subjected to hypo-osmotic shock and then restoration of isotonicity.

Immediately following restoration of isotonicity, the entire bag assembly was subjected to centrifugation (typically about 8 to about 10 minutes), followed by separation of the cells from the hemolysate. In so doing, the cells were exposed to hemolysate influence for a minimal period of time, i.e., approximately 10 minutes. Following centrifugation, the supernatant of the hemolysate in Bag 1 (or bag 5) was discarded, and fresh medium was added to Bag 1 (or bag 5), followed by incubation for about 1-2 hours at 37° C. Following incubation, the cells were subjected to a single wash step.

Comparative (Prior Art) Procedure

Following the teachings in Danon, the Buffy coat was subjected to hypo-osmotic shock immediately after processing the whole blood and separating it into its 3 main components, i.e., red blood cells, plasma, and the Buffy coat. Thus, in sharp contrast to the present invention, Danon's procedure does not entail incubation of the Buffy coat after separation of the main blood components and prior to subjecting the Buffy coat to hypo-osmotic shock. The hypo-osmotic shock was conducted while the Buffy coat was contained in Bag PB$_3$.

As a separate step, and after hypo-osmotic shock the buffered calcium chloride solution was transferred from Bag PB$_6$ to Bag PB$_2$ which contains the plasma, followed by deep-freezing the plasma in PB$_2$ for 10 minutes, and then placing it in a water bath at 37° C. for an additional 30 minute incubation period. During this time, the Buffy coat fraction which had been subjected to hypo-osmotic shock was allowed to stand wherein the leukocytes remained exposed to the hemolysate.

Following the conclusion of this coagulation process, which in total lasted about 40 minutes, the entire bag system was subject to centrifugation, and the hemolysate was discarded. Thus, the cells were exposed to the hemolysate for a period of at least about 55 minutes (i.e., which included the 40-minute standing period that coincided with the plasma coagulation, and an additional 15 minutes for centrifugation). In contrast, in the inventive method, the leukocytes were centrifuged immediately for about 5 min and thus were exposed to hemolysate for much less time, i.e., less than 10 minutes.

After the supernatant from PB$_3$ was discarded, fresh medium was added thereto, followed by transferring the entire suspension back to PB$_S$, which was then incubated for about 17 hours at 37° C. Following incubation, the cells were washed 3 times. In contrast, in the embodiments of the present invention, the incubation period was conducted in coagulated plasma for 1-2 hours, and washed only one time.

Until the aforesaid incubation was conducted, all prior steps were carried out in transfusion bags, which were the bags the whole blood was collected in. In contrast, the inventive embodiments entailed use of infusion bags which are usually used to administer intravenous solutions such as saline.

Danon's procedure was conducted 4 times and compared to the results generated by the embodiment of the present invention. The results, as set forth below, were averaged.

Results

The total amount of the white blood cells (leukocytes) obtained from a standard blood unit, calculated as a final concentration multiplied by final volume of cell suspension, was determined for each batch of whole blood. The averaged results for the 111 batches of whole blood processed according to the method of the present invention, and the 4 batches that were processed in accordance with the procedure disclosed in Danon, are set forth in Table 9.

TABLE 9

Yield of WBC per blood unit - (The present invention yielded ~90-fold higher amounts of WBCs.)

| Number of batches | WBC, ($\times 10^6$) | |
|---|---|---|
| | Average | SD |
| Present invention (n = 111) | 449 | 220 |
| Danon (n = 4) | 5 | 4 |

The results show that the method of the present invention resulted in about 90 times greater total number of leukocytes obtained from a standard blood unit (about 450 ml), as compared to Danon's procedure. More generally, the present method results in a yield of at least about $100 \times 10^6$, $125 \times 10^6$, $150 \times 10^6$, $175 \times 10^6$, $200 \times 10^6$, $225 \times 10^6$, $250 \times 10^6$, $275 \times 10^6$, $300 \times 10^6$, $325 \times 10^6$, $350 \times 10^6$, $375 \times 10^6$, $400 \times 10^6$, $425 \times 10^6$, $450 \times 10^6$, $475 \times 10^6$, $500 \times 10^6$, or higher leukocytes per standard blood unit (including all sub-ranges thereof).

The number of viable cells contained within the total cell population, expressed as a percentage, was measured by the Trypan Blue exclusion method. The cells were counted in a Newbauer hamemocytometer after suspension in Trypan Blue (1:1 ratio) for evaluation of cell count and percentage of viability. The results are presented in Table 10.

TABLE 10

| Procedure | Viability (% live cells) | |
|---|---|---|
| | Average | SD |
| Present invention (n = 111) | 98% | 0.02% |
| Danon (n = 4) | 77% | 6% |

The data in Table 10 show that in addition to the lower yield (as shown in Table 9), Danon's procedure resulted in cell suspension with significantly lower viability. That is, almost a quarter (i.e., 23%) of the preparation was composed of dead leukocytes (greater than a 10-fold higher percentage of dead cells). In sharp contrast, almost all of the white blood cells processed according to the inventive method were determined to be viable. More generally, the inventive ALC may contain at least 80%, 81%, 82%, 83%, 84%, 85%, 86%, 87%, 88%, 89%, 90%, 91%, 92%, 93%, 94%, 95%, 96%, 97%, 98% or greater, viable leukocytes based on this total number of leukocyte cells in the ALC (including all sub-ranges thereof).

Expression of the CD11b activation marker on granulocytes was measured by flow cytometry, and presented as a percentage of CD11b positive cells in granulocyte population (CD15 positive cells). Cells sampled from final product were co-stained with anti-CD11b conjugated to fluorescein isothiocynate (FITC) and anti-CD15 conjugated to phycoerythrin (PE), and analyzed using FACSCalibur flow cytometer (Becton Dickinson Immunocytometry Systems, San Jose, Calif., USA). CD 11b expression on granulocytes in cells from 81 final product batches performed in accordance with the inventive method, and from 3 final product batches produced according Danon's procedure, were analyzed.

TABLE 11

CD11b expression on Granulocytes

| Procedure | % of Granulocytes expressing CD11b activation marker | |
|---|---|---|
| | Average | SD |
| Present invention (n = 81) | 84.6 | 6.2 |
| Danon (n = 3) | 46.9 | 9.2 |

As shown by the data, the inventive method yielded almost two-fold higher activated granulocytes on a percentage basis as compared to Danon's procedure. More generally, the ALCs of the present invention may contain at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or higher, CD11b(+) granulocytes, relative to the total granulocyte population in the ALC (including all sub-ranges thereof).

The results of the comparative experimentation demonstrate that the presently disclosed invention achieves at least 3 unexpected results as compared to the process disclosed in Danon, namely, a greater yield of viable leukocytes, a high percentage of viable cells, and a higher level of granulocyte activation, as shown by higher expression of the CD11b activation marker. These increases are dramatic and unexpected.

List of Publications Cited In Application

J. Li, et al., *Pathophysiology of Acute Wound Healing*. Clinical Dermatol. 2007 January-February; 25(1):9-18.

G. Broughton 2nd, et al., Wound Healing: An Overview. Plast Reconstr Surg. 2006 June; 117(7 Suppl):1e-S-32e-S.

AK Tsirogianni, et al., *Wound Healing: Immunological Aspects*. Injury. 2006 April; 37 Suppl 1:S5-12. Epub 2006.

AJ Singer, et al., *Cutaneous Wound Healing*. New Eng. J. Med. 1999; 341(10):738-46.

P. Martin, *Wound Healing—Aiming For Perfect Skin Regeneration*. Science 1997; 276(5309):75-81.

AD Agaiby, et al., *Immuno-Inflammatory Cell Dynamics During Cutaneous Wound Healing*. J. Anat. 1999 November; 195 (Pt 4):531-42.

DWH Riches, *Macrophage Involvement In Wound Repair, Remodeling and ®brosis. In The Molecular and Cellular*

*Biology of Wound Repair*, (1996) lnd edn (ed. Clark RAF), pp. 95±141. New York, London: Plenum Press.

D. Greiling, et al., *Fibronectin Provides a Conduit for Fibroblast Transmigration from Collagenous Stroma into Fibrin Clot Provisional Matrix*. J. Cell. Sci. 1997; 110:861-70.

MG Tonnesen, et al., *Angiogenesis In Wound Healing*. J. Investig. Dermatol. Symp. Proc. 2000; 5(1):40-6.

JP Kim, et al., *Mechanisms of Human Keratinocyte Migration on Fibronectin: Unique Role of RGD Site and Integrins*. J. Cell. Physiol. 1992; 151:443-50.

JJ Tomasek et al., *Myofibroblasts and Mechano-Regulation of Connective Tissue Remodelling*. Nat. Rev. Mol. Cell. Biol. (2002) 3:349-363.

S Werner, et al., *Regulation of Wound Healing by Growth Factors and Cytokines*. Physiol Rev. 2003 July; 83(3):835-70.

D. A. Keen, *Review of Research Examining the Regulatory Role of Lymphocytes in Normal Wound Healing*. J. Wound Care. 2008.

J Jameson, et al., *A Role for Skin—T Cells in Wound Repair*. Science 296: 747-749, 1992.

W L Havran, et al., *Epithelial Cells and Their Neighbors. III. Interactions Between Intraepithelial Lymphocytes and Neighboring Epithelial Cells*. Am. J. Physiol. Gastrointest Liver Physiol. 2005 October; 289(4):G627-30.

J Parkin, et al., *An Overview of the Immune System*. Lancet. 2001; 357:1777-1789.

A Moretta, et al., *Human NK Cells: From HLA Class I-Specific Killer Ig-like Receptors to the Therapy of Acute Leukemias*. Immunol. Rev. 2008 August; 224:58-69.

BM Doshi, et al., *Wound Healing From a Cellular Stress Response Perspective*. Cell Stress Chaperones. 2008 December; 13(4):393-9.

G J Moran, et al., *Antimicrobial Prophylaxis for Wounds and Procedures in the Emergency Department*. Infect. Dis. Clin. North Am. 2008.

MA Fonder, et al., *Treating the Chronic Wound: A Practical Approach to the Care of Nonhealing Wounds and Wound Care Dressings*. J. Am. Acad. Dermatol. 2008 February; 58(2):185-206.

JA Thackham, et al., *The Use of Hyperbaric Oxygen Therapy to Treat Chronic Wounds: A Review*. Wound Repair Regen. 2008, 1998 May-June; 16(3):321-30.

D R Berlowitz, et al., *Are all pressure ulcers the result of deep tissue injury? A Review of the Literature*. Ostomy Wound Manage. 2007 October; 53(10):34-8.

K. Girouard, et al., *The symptom of pain with pressure ulcers: a review of the literature*. Ostomy Wound Manage. 2008 May; 54(5):30-40, 32.

All publications cited in the specification, including patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for making an activated leukocyte composition comprising:
   a) incubating human leukocytes for a period of time so that the leukocytes transition from a quiescent to a functionally active state;
   b) subjecting the leukocytes to hypo-osmotic shock; and
   c) adding to the leukocytes of step b) a salt solution in an amount which restores isotonicity.

2. The method of claim 1, further comprising mixing the activated leukocytes of step c) with serum.

3. The method of claim 1, wherein the incubation of step a) occurs at a temperature of about 12° C. to about 28° C. for a time ranging from about 8 to about 20 hours.

4. The method of claim 3, wherein the incubation of step a) occurs at a temperature of about 18° C. to about 24° C. for a time ranging from about 8 to about 12 hours.

5. The method of claim 1, wherein the incubation of step a) occurs at a temperature of 12° C. to about 28° C. for a time ranging from about 90 minutes, 2 hours, 3 hours, 4 hours, 5 hours, 6 hours, 7 hours, 8 hours, or 12 hours to about 20 hours.

6. The method of claim 1, wherein the incubation of step a) occurs at a temperature up to about 37° C. and for a time ranging from five hours to about 24 hours.

7. The method of claim 1, wherein the activated leukocyte composition has a shelf life extending up to 97 hours following collection of the human leukocytes.

8. The method of claim 1, wherein the human leukocytes are obtained from a donor having an O negative blood type.

9. The method of claim 1, wherein the hypo-osmotic shock comprises contacting the leukocytes with water.

10. The method of claim 2, wherein the serum is prepared from plasma obtained from a donor having AB positive blood type.

11. The method of claim 2, wherein the mixture of activated leukocytes and serum is incubated at about 37° C. for about 8-20 hours.

12. The method of claim 11, wherein the mixture of activated leukocytes and serum is incubated for about 60 to about 120 minutes.

* * * * *